(12) United States Patent
Ren et al.

(10) Patent No.: US 7,151,096 B2
(45) Date of Patent: Dec. 19, 2006

(54) CYCLIC COMPOUNDS AND COMPOSITIONS AS PROTEIN KINASE INHIBITORS

(75) Inventors: Pingda Ren, San Diego, CA (US); Francisco Adrian, San Diego, CA (US); Nathanael S. Gray, San Diego, CA (US); Xia Wang, San Diego, CA (US)

(73) Assignee: IRM LLC, Hamilton (BM)

( * ) Notice: Subject to any disclaimer, the term of this patent is extended or adjusted under 35 U.S.C. 154(b) by 67 days.

(21) Appl. No.: 10/794,454

(22) Filed: Mar. 5, 2004

(65) Prior Publication Data

US 2004/0235841 A1  Nov. 25, 2004

Related U.S. Application Data

(60) Provisional application No. 60/452,633, filed on Mar. 5, 2003.

(51) Int. Cl.
*C07D 471/21*  (2006.01)
*C07D 259/00*  (2006.01)
*A61K 31/395*  (2006.01)

(52) U.S. Cl. .................. 514/183; 514/273; 540/460

(58) Field of Classification Search ................ 540/460; 514/183, 273
See application file for complete search history.

*Primary Examiner*—Bruck Kifle
(74) *Attorney, Agent, or Firm*—Genomics Institute of the Novartis Research Foundation; Scott W Reid

(57) ABSTRACT

The invention provides a novel class of cyclic compounds, pharmaceutical compositions comprising such cyclic compounds and methods of using such compounds to treat or prevent diseases and disorders associated with cyclin-dependent kinases (CDKs) activity, particularly diseases associated with the activity of CDK2 and CDK5.

8 Claims, No Drawings

CYCLIC COMPOUNDS AND COMPOSITIONS AS PROTEIN KINASE INHIBITORS

CROSS-REFERENCE TO RELATED APPLICATIONS

This application claims the benefit of priority to U.S. Provisional Patent Application No. 60/452,633 (filed Mar. 5, 2003). The full disclosure of this application is incorporated herein by reference in its entirety and for all purposes.

BACKGROUND OF THE INVENTION

1. Field of the Invention

The invention provides a novel class of cyclic compounds, pharmaceutical compositions comprising such cyclic compounds and methods of using such compounds to treat or prevent diseases and disorders associated with cyclin-dependent kinases (CDKs) activity, particularly diseases associated with the activity of CDK2 and CDK5.

2. Background

The cyclin-dependent protein kinases (CDKs) are a group of serine/threonine kinases (STKs) that control the progression of cells through the cell cycle. Cyclins are small regulatory proteins that act by binding to and activating CDKs that then trigger various phases of the cell cycle by phosphorylating and activating selected proteins involved in the mitotic process. In addition to the binding of cyclin, CDK activation requires the phosphorylation of a specific threonine residue and the dephosphorylation of a specific tyrosine residue. CDK2 is essential for normal cell cycling and plays a critical role in disorders arising from abnormal cell cycling, a common characteristic of many oncological disorders. Inhibitors of CDK2 are therefore useful for the treatment of various types of proliferative diseases such as cancer and other diseases or conditions associated with abnormal cell growth.

CDK5, unlike other CDKs, is not involved in cell cycle progression control and is not activated upon association with a cyclin. CDK5 is active in neuronal cells upon association with a 35 kD protein (p35) or a proteolytic fragment of p35(p25). Under physiological conditions, CDK5 is involved in neuron development and, under pathological conditions, CDK5 is responsible for the hyperphosphorylation of the microtubule associated protein, tau. CDK5 also phosphorylates dopamine and cyclic APM-regulated Phosphorprotein (DARPP-32) at threonine 75 and is thus indicated in having a role in dopaminergic neurotransmission. Consequently, CDK5 along with its cofactor p35 or p25 has been linked to neurodegenerative disorders and inhibitors of CDK/p35 or CDK5/p25 are therefore useful for the treatment of neurodegenerative disorders such as Alzheimer's disease, Parkinson's disease, Huntington's disease or stroke.

Therefore, the novel compounds of this invention are useful in the therapy of proliferative diseases such as cancer, inflammation, arthritis, cardiovascular disease and neurodegenerative disorders such as Alzheimer's disease, Parkinson's disease, stroke, or Huntington's disease. These compounds also are useful in the treatment of topical and systemic fungal infections.

SUMMARY OF THE INVENTION

This application relates to compounds of Formula I:

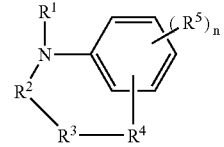

in which n is chosen from 0, 1, 2 and 3;

$R^1$ is chosen from hydrogen and $C_{1-10}$alkyl;

$R^2$ is chosen from $C_{6-10}$arylene and $C_{5-10}$heteroarylene; wherein any aryl or heteroaryl of $R^2$ is optionally substituted by one to three radicals chosen from halo, $C_{1-10}$alkyl, halo-substituted $C_{1-4}$alkyl, $C_{1-10}$alkoxy and halo-substituted $C_{1-4}$alkoxy;

$R^3$ is chosen from $C_{6-10}$arylene and $C_{5-10}$heteroarylene; wherein any aryl or heteroaryl of $R^3$ is optionally substituted by one to three radicals chosen from halo, $C_{1-10}$alkyl, halo-substituted $C_{1-4}$alkyl, $C_{1-10}$alkoxy and halo-substituted $C_{1-4}$alkoxy;

$R^4$ is chosen from —$XNR^6(CH_2)_mNR^7C(O)$—, —$XNR^6(CH_2)_mNR^7C(O)CH_2$—, $XNR^6(CH_2)_mNR^7(CH_2)_mNR^7C(O)$—, —$O(CH_2)_mNR^7C(O)$—, $XNR^6(CH_2)_mO$— and —$XNR^6(CH_2)_mNR^7CH_2$—; wherein X is a bond or $C_{1-4}$alkylene; m is chosen from 1, 2, 3, 4, 5 and 6; $R^6$ and $R^7$ independently are chosen from hydrogen and $C_{1-10}$alkyl; and $R^5$ is chosen from halo, $C_{1-10}$alkyl, halo-substituted $C_{1-4}$alkyl, $C_{1-10}$alkoxy and halo-substituted $C_{1-4}$alkoxy and heterocycloalkyl; wherein any heterocycloalkyl of $R^5$ is optionally substituted with a group chosen from halo, $C_{1-6}$alkyl, halo-substituted $C_{1-4}$alkyl, $C_{1-10}$alkoxy, halo-substituted $C_{1-4}$alkoxy, heterocycloalkyl-$C_{1-4}$alkyl and —$XNR^8R^9$, wherein X is a bond or $C_{1-4}$alkylene; $R^8$ and $R^9$ are independently chosen from hydrogen and $C_{1-10}$alkyl optionally substituted by halo or amino; and the N-oxide derivatives, prodrug derivatives, protected derivatives, individual isomers and mixtures of isomers thereof; and the pharmaceutically acceptable salts and solvates (e.g. hydrates) of such compounds.

A second aspect of the invention is a pharmaceutical composition which contains a compound of Formula I or an N-oxide derivative, individual isomer or mixture of isomers thereof, or a pharmaceutically acceptable salt thereof, in admixture with one or more suitable excipients.

A third aspect of the invention is a method for treating a disease in an animal in which inhibition of CDK5 and/or CDK2 activity can prevent, inhibit or ameliorate the pathology and/or symptomology of the disease, which method comprises administering to the animal a therapeutically effective amount of a compound of Formula I or a N-oxide derivative, individual isomer or mixture of isomers thereof; or a pharmaceutically acceptable salt thereof.

A fourth aspect of the invention is the use of a compound of Formula I in the manufacture of a medicament for treating a disease in an animal in which CDK5 and/or CDK2 activity contributes to the pathology and/or symptomology of the disease.

A fifth aspect of the invention is a process for preparing compounds of Formula I and the N-oxide derivatives, prodrug derivatives, protected derivatives, individual isomers and mixtures of isomers thereof; and the pharmaceutically acceptable salts thereof.

DESCRIPTION OF THE PREFERRED EMBODIMENTS

The invention provides compounds that are useful in the treatment and/or prevention of diseases or disorders mediated by kinase activity. Also provided are methods for treating such diseases or disorders.

Definitions

In this specification, unless otherwise defined:

"Alkyl" as a group and as a structural element of other groups, for example halo-substituted-alkyl, alkoxy, acyl, alkylthio, alkylsulfonyl and alkylsulfinyl, can be either straight-chained or branched. "Alkenyl" as a group and as a structural element of other groups contains one or more carbon-carbon double bonds, and can be either straight-chain, or branched. Any double bonds can be in the cis- or trans-configuration. A preferred alkenyl group is vinyl. "Alkynyl" as a group and as structural element of other groups and compounds contains at least one C≡C triple bond and can also contain one or more C=C double bonds, and can, so far as possible, be either straight-chain or branched. A preferred alkynyl group is propargyl. Any cycloalkyl group, alone or as a structural element of other groups can contain from 3 to 8 carbon atoms, preferably from 3 to 6 carbon atoms. Alkoxy includes, for example, methoxy, ethoxy, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. For example, arylene as used in this application can be phenylene or naphthylene, preferably phenylene, more preferably 1,4-phenylene.

"Halo" or "halogen" means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl. Halo-substituted alkoxy includes, for example, trifluoromethoxy.

"Heteroaryl" means aryl, as defined in this application, provided that one or more of the ring carbon atoms indicated are replaced by a hetero atom moiety selected from N, O or S, and each ring is comprised of 5 to 6 ring atoms, unless otherwise stated. For example, heteroaryl as used in this application includes thiazolyl, thiophenyl, pyrimidinyl, pyrazolyl, pyridinyl, furanyl, isoxazolyl, benzoxazolyl or benzo[1,3]dioxolyl, preferably pyrimidinyl, thiophenyl, furanyl or pyridinyl. "Heteroarylene" means heteroaryl, as defined in this application, provided that the ring assembly comprises a divalent radical.

DETAILED DESCRIPTION OF THE INVENTION

The invention provides compounds that are useful for treating or preventing diseases or disorders that are mediated by kinase activity.

In one embodiment, with reference to compounds of Formula I, n is chosen from 0, 1 or 2; $R^1$ is chosen from hydrogen and $C_{1-4}$alkyl; $R^2$ is $C_{5-6}$heteroarylene; $R^3$ is $C_{5-6}$heteroarylene optionally substituted by one to three radicals chosen from halo, $C_{1-10}$alkyl, halo-substituted $C_{1-4}$alkyl; $R^4$ is chosen from —NR$^6$(CH$_2$)$_m$NR$^7$C(O)—, —NR$^6$(CH$_2$)$_m$NR$^7$C(O)CH$_2$—, —O(CH$_2$)$_m$NR$^7$C(O)—, —NR$^6$(CH$_2$)$_m$O— and —NR$^6$(CH$_2$)$_m$NR$^7$CH$_2$—; wherein m is chosen from 1, 2, 3, 4 and 5; $R^6$ and $R^7$ independently are chosen from hydrogen and $C_{1-10}$alkyl; and $R^5$ is chosen from halo, $C_{1-10}$alkyl, heterocycloalkyl optionally substituted with $C_{1-6}$alkyl, heterocycloalkyl-$C_{1-4}$alkyl and —NR$^8$R$^9$, wherein $R^8$ is hydrogen and $R^9$ is $C_{1-4}$alkyl optionally substituted by halo or amino.

In another embodiment, n is chosen from 0 and 1; $R^1$ is hydrogen; $R^2$ is a group chosen from formula (a), (b), (c) and (d):

(a)

(b)

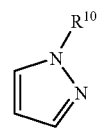

(c)

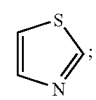

(d)

wherein $R^{10}$ is chosen from hydrogen and $C_{1-4}$alkyl; $R^3$ is chosen from formula (a) and (b):

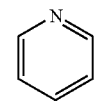

(a)

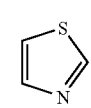

(b)

optionally substituted by halo-substituted $C_{1-4}$alkyl; $R^4$ is chosen from —NH(CH$_2$)$_m$NHC(O)—, —NH(CH$_2$)$_m$NHC(O)CH$_2$—, —O(CH$_2$)$_m$NHC(O)—, NH(CH$_2$)$_m$O— and —NH(CH$_2$)$_m$NHCH$_2$—; wherein m is chosen from 1, 2, 3, 4 and 5; and $R^5$ is chosen from halo, $C_{1-10}$alkyl, piperazinyl optionally substituted with $C_{1-4}$alkyl, morpholino-methyl and —NR$^9$R$^{10}$, wherein $R^9$ is hydrogen and $R^{10}$ is ethyl optionally substituted by amino.

In another embodiment, compounds are of formula Ia:

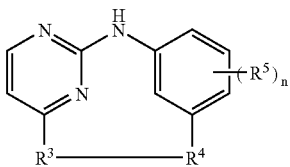

in which n is 0 or 1; R³ is chosen from formula (a) and (b):

(a)

(b)

optionally substituted by halo-substituted $C_{1-4}$alkyl; $R^4$ is chosen from —NH(CH$_2$)$_m$NHC(O)—, —NH(CH$_2$)$_m$NH(CH$_2$)$_m$NHC(O)—, —NH(CH$_2$)$_m$NHC(O)CH$_2$—, —O(CH$_2$)$_m$NHC(O)—, —NH(CH$_2$)$_m$O— and —NH(CH$_2$)$_m$NHCH$_2$—; wherein m is chosen from 1, 2, 3, 4 and 5; and $R^5$ is chosen from halo, $C_{1-10}$alkyl, piperazinyl optionally substituted with $C_{1-4}$alkyl, morpholino-methyl or —NR⁹R¹⁰, wherein R⁹ is hydrogen and R¹⁰ is ethyl optionally substituted by amino.

In another embodiment, compounds are of formula Ib:

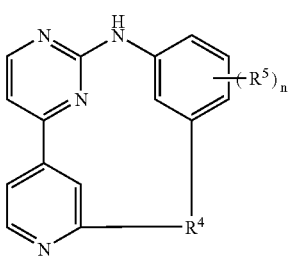

in which n is 0 or 1; R⁴ is chosen from —NH(CH$_2$)$_m$NHC(O)—, —NH(CH$_2$)$_m$NHC(O)CH$_2$—, —O(CH$_2$)$_m$NHC(O)—, —NH(CH$_2$)$_m$O— and —NH(CH$_2$)$_m$NHCH$_2$—; wherein m is 1, 2, 3, 4 or 5; and R⁵ is chosen from halo, $C_{1-10}$alkyl, piperazinyl optionally substituted with $C_{1-4}$alkyl, morpholino-methyl or —NR⁹R¹⁰, wherein R⁹ is hydrogen and R¹⁰ is ethyl optionally substituted by amino.

In a further embodiment, n is 0 or 1; R⁴ is chosen from —NH(CH$_2$)$_m$NHC(O)—, —NH(CH$_2$)$_m$NHC(O)CH$_2$—, —O(CH$_2$)$_m$NHC(O)—, —NH(CH$_2$)$_m$O— and —NH(CH$_2$)$_m$NHCH$_2$—; wherein m is 2, 3, 4 or 5; and R⁵ is chosen from bromo, chloro, fluoro, methyl, piperazinyl optionally substituted with methyl, morpholino-methyl or —NH(CH$_2$)$_2$NH$_2$.

Preferred compounds of Formula I are detailed in the examples and Table I, infra.

The invention provides forms of the compound that have the hydroxyl or amine group present in a protected form; these function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes. The present invention also includes both the enzymatically phosphorylated or dephosphorylated compounds of Formula I, optionally in equilibrium.

Compounds of Formula I can exist in free form or in salt form, e.g. addition salts with inorganic or organic acids, e.g. an ammonium salt or salts with metals such as lithium, sodium, potassium, calcium, zinc or magnesium, or a mixture thereof. Compounds of Formula I and their salts in hydrate or solvate form are also part of the invention.

When the compounds of Formula I have asymmetric centers in the molecule, various optical isomers are obtained. The present invention also encompasses enantiomers, racemates, diastereoisomers and mixtures thereof. Moreover, when the compounds of Formula I include geometric isomers, the present invention embraces cis-compounds, trans-compounds and mixtures thereof. Similar considerations apply in relation to starting materials exhibiting asymmetric carbon atoms or unsaturated bonds as mentioned above.

Methods for Preparing Kinase Inhibitors

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

Compounds of Formula I, wherein R⁴ is —NR⁶(CH$_2$)$_m$NR⁷CO(CH$_2$)$_{0-1}$—, can be prepared by proceeding as in the following Reaction scheme 1:

Reaction Scheme 1

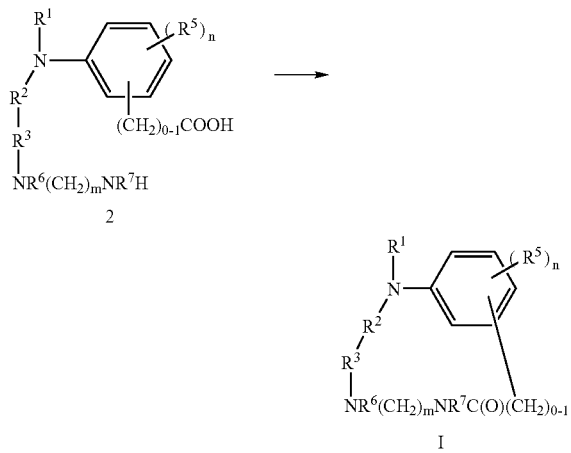

in which n, m, $R^1$, $R^2$, $R^3$, $R^5$, $R^6$ and $R^7$ are as defined for Formula I above.

Compounds of formula I can be prepared by condensing the acid and amine moieties of a compound of formula 2. The condensation reaction can be effected in an appropriate solvent (e.g., DMF), optionally with a coupling reagent (e.g., HATU), and base (e.g., diisopropylethylamine) at a temperature range of about 0 to about 25° C. and requires from about 2 to about 10 hours to complete.

Compounds of Formula I, wherein $R^4$ is —O(CH$_2$)$_m$NR$^7$CO(CH$_2$)$_{0-1}$—, can be prepared by proceeding as in the following Reaction scheme 2:

Reaction Scheme 2

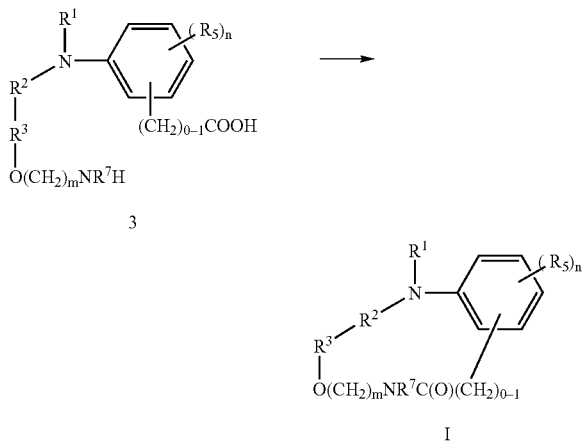

in which n, m, $R^1$, $R^2$, $R^3$, $R^5$ and $R^7$ are as defined for Formula I above.

Compounds of formula I can be prepared by condensing the acid and amine moieties of a compound of formula 3. The condensation reaction can be effected in an appropriate solvent (e.g., DMF), optionally with a coupling reagent (e.g., HATU), and base (e.g., diisopropylethylamine) at a temperature range of about 0 to about 25° C. and requires from about 2 to about 10 hours to complete.

Compounds of Formula I, wherein $R^4$ is —NR$^6$(CH$_2$)$_m$O—, can be prepared by proceeding as in the following Reaction scheme 3:

Reaction Scheme 3

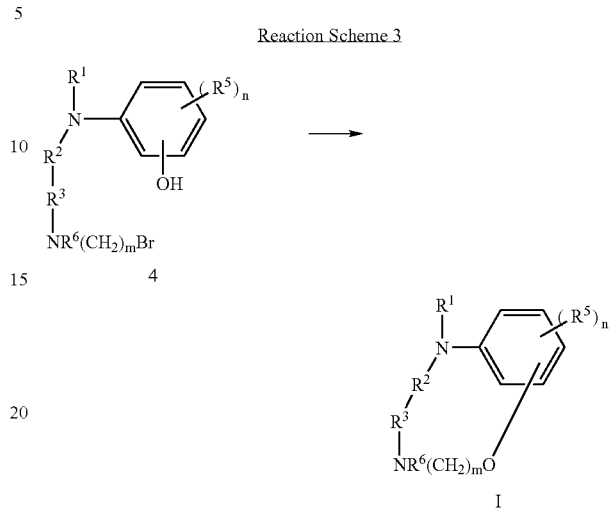

in which n, m, $R^1$, $R^2$, $R^3$, $R^5$ and $R^6$ are as defined for Formula I above.

Compounds of formula I can be prepared by reacting the hydroxyl and alkyl-halo moieties of a compound of formula 4. The reaction can be effected in an appropriate solvent (e.g., acetone) in the presence of an appropriate base (e.g., potassium carbonate) at reflux temperatures and requires from about 2 to about 10 hours to complete.

Compounds of Formula I, wherein $R^4$ is —NR$^6$(CH$_2$)$_m$O—, can be prepared by proceeding as in the following Reaction scheme 4:

Reaction Scheme 4

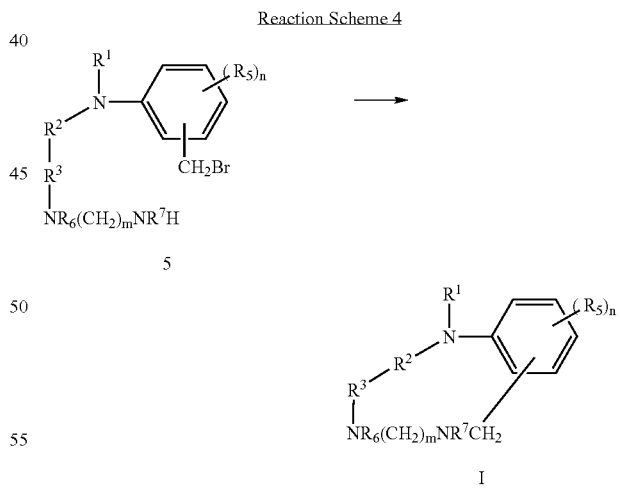

in which n, m, $R^1$, $R^2$, $R^3$, $R^5$, $R^6$ and $R^7$ are as defined for Formula I above.

Compounds of formula I can be prepared by reacting the amine and alkyl-halo moieties of a compound of formula 5.

Additional Processes for Preparing Compounds of the Invention:

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at about 0 to about 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) cyclizing a compound of Formula 2, 3, 4 or 5:

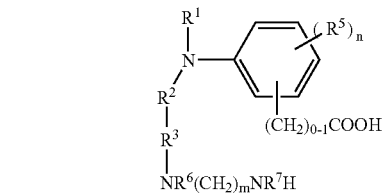

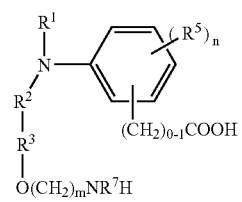

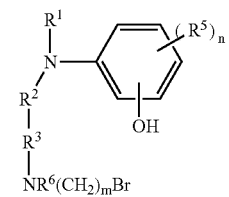

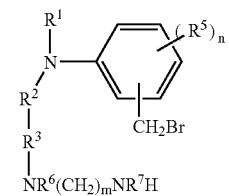

in which m, n, $R^1$, $R^2$, $R^3$, $R^5$, $R^6$ and $R^7$ are as defined in the Summary of the Invention; or (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

Methods and Pharmaceutical Compositions for Treating CDK Related Conditions

The compounds of Formula I in free form or in pharmaceutically acceptable salt form, exhibit valuable pharmacological properties, for example, as indicated by the in vitro tests of Example 39 and are therefore indicated for therapy of diseases and disorders associated with altered CDK activity. For CDK5, compounds of Formula I preferably show an $IC_{50}$ in the range of $1\times10^{-10}$ to $1\times10^{-5}$ M, preferably less than 1 µM. Compounds of Formula I preferably show an inhibition of CDK2 activity of greater than 50% and demonstrate a lack of cellular toxicity.

This invention also provides a method for preventing or treating diseases or conditions comprising abnormal cell growth in a mammal, including a human, comprising administering to the mammal a compound of Formula I in an amount effective to inhibit CDK2 activity. Such diseases or conditions include, for example, cancer. The cancer may be a carcinoma, for example carcinoma of the bladder, breast, colon, kidney, liver, lung, for example small cell lung cancer, esophagus, gall bladder, ovary, pancreas, stomach, cervix, thyroid, prostate, or skin, for example squamous cell carcinoma; a hematopoietic tumor of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukemias, myelodyplastic syndrome, or promyelocytic leukemia; a tumor of mesenchymal origin, for example fibrosarcoma or rhabdomyosarcoma; a tumor of the central or peripheral nervous system, for example astrocytoma, neuroblastomas, glioma or schwannoma; melanoma; seminoma; teratocarcinoma; osteosarcoma; xenoderoma pigmentoum; keratoctanthoma; thyroid follicular cancer; or Kaposi's sarcoma. Diseases or conditions comprising benign abnormal cell growth include benign prostate hyperplasia, familial adenomatosis polyposis, neuro-fibromatosis, atherosclerosis, pulmonary fibrosis, arthritis, psoriasis, glomerulonephritis, restenosis, hypertrophic scar formation, inflammatory bowel disease, transplantation rejection, fungal infection, and endotoxic shock.

This invention also provides a method for treating a neurodegenerative disease or condition in a mammal, including a human, comprising administering to the mammal a compound of Formula 1 in an amount effective in treating said disease or condition. Such neurodegenerative diseases or conditions include, for example, Huntington's disease, stroke, spinal cord trauma, traumatic brain injury, multiinfarct dementia, epilepsy, amyotrophic lateral sclerosis, pain, viral induced dementia for example AIDS induced dementia, neurodegeneration associated with bacterial infection, migraine, hypoglycemia, urinary incontinence, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progressive supranuclear palsy, lower lateral sclerosis, and subacute sclerosing panencephalistis.

This invention also provides a method for treating a disease or condition the treatment of which can be effected or facilitated by altering dopamine mediated neurotransmission in a mammal, including a human, comprising administering to the mammal a compound of Formula 1 in an amount effective in treating said disease or condition. Such diseases or conditions include, for example, Parkinson's disease; schizophrenia; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; personality disorder of the schizoid type; drug addiction, including narcotic (e.g. heroin, opium, and morphine), cocaine and alcohol addiction; drug withdrawal, including narcotic, cocaine and alcohol withdrawal; obsessive compulsive disorder; Tourette's syndrome; depression; a major depressive episode, a manic or mixed mood episode, a hypomanic mood episode, a depressive episode with atypical features or with melancholic features or catatonic features, a mood episode with postpartum onset; post-stroke depression, major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example bipolar I disorder, bipolar II disorder, cyclothymic disorder; anxiety; attention deficit and hyperactivity disorder; and attention deficit disorder.

The required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of Formula I can be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form. Pharmaceutical compositions comprising a compound of Formula I in free form or in pharmaceutically acceptable salt form in association with at least one pharmaceutical acceptable carrier or diluent can be manufactured in conventional manner by mixing with a pharmaceutically acceptable carrier or diluent.

The compounds of Formula I can be administered in free form or in pharmaceutically acceptable salt form, for example, as indicated above. Such salts can be prepared in a conventional manner and exhibit the same order of activity as the free compounds.

Also provided by the invention are compounds of Formula I, in free form or in a pharmaceutically acceptable salt form for use in treatment of conditions such as those described above. Pharmaceutical compositions, that includes a compound of Formula I in free form or in pharmaceutically acceptable salt form, in association with a pharmaceutically acceptable diluent or carrier thereof are also provided by the invention.

Also provided by the invention are methods involving co-administration, e.g. concomitantly or in sequence, of a therapeutically effective non-toxic amount of a compound of Formula I and at least a second drug substance. For example, the compounds of Formula I can be administered as the sole active ingredient or in conjunction with, e.g. as an adjuvant to, other drugs e.g. a COX-II inhibitor, an anti-depressant or anxiolytic compound, a NK-1 receptor antagonist, a $5HT_{1D}$ receptor antagonist, a SSRI, an antipsychotic compound, an acetyl cholinesterase inhibitor, a tissue plasminogen activator, a neutrophil inhibitory factor, a NMDA receptor antagonist or a potassium channel modulator.

Where the compounds of Formula I are administered in conjunction with other therapies, dosages of the co-administered compounds will of course vary depending on the type of co-drug employed, on the specific drug employed, on the condition being treated and so forth.

Also provided by the invention are pharmaceutical combinations, e.g. a kit, comprising a) a first agent which is a compound of Formula I as disclosed herein, in free form or in pharmaceutically acceptable salt form, and b) at least one co-agent, e.g. a COX-II inhibitor, an anti-depressant or anxiolytic compound, a NK-1 receptor antagonist, a $5HT_{1D}$ receptor antagonist, a SSRI, an antipsychotic compound, an acetyl cholinesterase inhibitor, a tissue plasminogen activator, a neutrophil inhibitory factor, a NMDA receptor antagonist or a potassium channel modulator. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

EXAMPLES

The following examples provide detailed descriptions of the preparation of representative compounds and are offered to illustrate, but not to limit the present invention.

Example 1

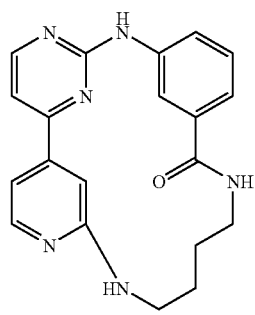

Nitric acid (70%, 6.66 mL) is added to a mixture of 3-amino benzoic acid ethyl ester (17.21 g, 104 mmol) and cyanamide (50% in water, 12.1 mL, 156 mmol) in 50 mL of ethanol. The reaction mixture is heated for 24 hours under reflux. It is then cooled to room temperature and filtered. The solid is washed with water, ether and dried to give 3-ethoxy-carbonyl-phenyl-guanidine nitrite as a gray solid; ESI-MS (m/z): 208.1 ($M^+$-$HNO_3$+H).

3-Dimethylamino-1-(2-chloro-4-pyridyl)-2-propen-1-one: A suspension of 2-chloroisonicotinic acid (15.7 g, 100 mmol) in DCM (40 mL) is added to oxalyl chloride (2M in DCM, 60 mL) at room temperature in the presence of DMF (0.2 mL). After stirring at room temperature for 2.5 hours, the mixture is concentrated. The residue is used for next reaction.

Triethyl amine (56 mL, 400 mmol) is added to a mixture of N,O-dimethylhydroxylamine hydrochloride (19.5 g, 200 mmol) in DCM (200 mL). After stirring for 10 minutes at room temperature, the reaction mixture is filtered. The filtrate is cooled to 0° C. and added to the above residue. The mixture is stirred at room temperature for 2 hours, washed with water (200 mL) and the aqueous is extracted with DCM (2×100 mL). The combined organic layers are washed with brine (2×150 mL) and dried over sodium sulfate, filtered and concentrated under reduced pressure to give 2-chloro-N-methoxy-N-methyl-isonicotinamide, which is used for the next reaction without further purification.

To a solution of 2-chloro-N-methoxy-N-methyl-isonicotinamide (20 g, 100 mmol) in THF (100 mL) is added a solution of methyl magnesium bromide (3M in THF, 73 mL, 220 mmol) at −40° C. After stirring the mixture for 2 hours at this temperature, the mixture is quenched with ice-cooled saturated ammonium chloride solution (300 mL). The organic phase is separated. The aqueous layer is extracted with ethyl acetate (2×150 mL). The combined organic layers are washed with brine and dried over sodium sulfate, filtered and concentrated under reduced pressure to give 4-acetyl-2-chloro-pyridine (14.4 g), which is used for the next reaction without further purification; ESI-MS (m/z): 156.0 ($M^+$+H).

A mixture of 4-acetyl-2-chloro-pyridine (1.72 g, 11 mmol) in N,N-dimethyl formamide diethyl acetal (10 mL) is heated to reflux for 1 hour and cooled to room temperature before adding hexane (8 mL). The solid is collected by filtration, washed with hexane and dried to give 3-dimethylamino-1-(2-chloro-4-pyridyl)-2-propen-1-one (1.70 g); ESI-MS (m/z): 211.0 ($M^+$+H).

N-[3-ethoxycarbonyl-phenyl]-4-(2-chloro-4-pyridyl)-2-pyrimidineamine: A mixture of 3-dimethylamino-1-(2-chloro-4-pyridyl)-2-propen-1-one (1.72 g, 8.18 mmol), 3-ethoxycarbonyl-phenyl-guanidine nitrite (2.21 g, 8.18 mmol), sodium hydroxide (0.327 g, 8.18 mmol) in 2-butanol (40 mL) is heated to reflux for 24 hours before cooling to room temperature with the addition of water (40 mL). The solid is collected by filtration, washed with water and 2-propanol, and dried to give N-[3-ethoxycarbonyl-phenyl]-4-(2-chloro-4-pyridyl)-2-pyrimidineamine (2.06 g); ESI-MS (m/z): 355.1 ($M^+$+H).

N-[3-carboxy-phenyl]-4-(2-chloro-4-pyridyl)-2-pyrimidineamine: A mixture of N-[3-ethoxycarbonyl-phenyl]-4-(2-chloro-4-pyridyl)-2-pyrimidineamine (860 mg, 2.43 mmol), lithium hydroxide (233 mg, 9.70 mmol) in ethanol (20 mL) and water (5 mL) is heated to reflux for 1 hour before cooling to room temperature. The mixture is concentrated, dissolved in water and acidified with 10% hydrochloric acid. The solid is collected by filtration and washed with water, methanol and dried to give N-[3-carboxy-phenyl]-4-(2-chloro-4-pyridyl)-2-pyrimidineamine (760 mg); ESI-MS (m/z): 327.0 ($M^+$+H).

N-[3-carboxy-phenyl]-4-[2-(4-amino-butyl-amino)-4-pyridyl]-2-pyrimidine-amine: A mixture of N-[3-carboxy-phenyl]-4-(2-chloro-4-pyridyl)-2-pyrimidineamine (99 mg, 0.30 mmol) in 1,4-diaminobutane (1.5 mL) is heated to 110° C. overnight, cooled to room temperature and concentrated.

The residue is dissolved in water and neutralized with 10% hydrochloric acid. The reaction mixture is purified by preparative HPLC to give N-[3-carboxy-phenyl]-4-[2-(4-amino-butyl-amino)-4-pyridyl]-2-pyrimidineamine (84 mg); ESI-MS (m/z): 379 (M⁺+H).

Macro-cyclization of N-[3-carboxy-phenyl]-4-[2-(4-amino-butyl-amino)-4-pyridyl]-2-pyrimidineamine: N-[3-carboxy-phenyl]-4-[2-(4-amino-butyl-amino)-4-pyridyl]-2-pyrimidineamine (35 mg, 0.09 mmol) is dissolved in DMF (50 mL) and then treated with diisopropylethylamine (60 µL, 0.32 mmol). This solution is cooled to 0° C., and treated with HATU (50 mg, 0.12 mmol). After stirring for 3 hours, the reaction mixture is concentrated and purified by preparative HPLC to give the desired macrocyclic compound; ESI-MS (m/z): 361 (M⁺+H).

Example 2

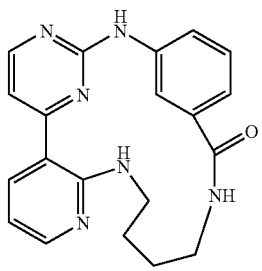

N-[3-ethoxycarbonyl-phenyl]-4-(2-chloro-3-pyridyl)-2-pyrimidineamine: A mixture of 3-dimethylamino-1-(2-chloro-3-pyridyl)-2-propen-1-one (810 mg, 3.86 mmol), 3-ethoxycarbonyl-phenyl-guanidine nitrite (1.07 g, 3.96 mmol), lithium hydroxide (105 mg, 4.38 mmol) in 2-butanol (20 mL) is heated to reflux overnight. The reaction mixture is cooled to room temperature, the solvent is removed and water (40 mL) is added. The solid is collected by filtration and washed with water, isopropanol and dried to give N-[3-ethoxycarbonyl-phenyl]-4-(2-chloro-3-pyridyl)-2-pyrimidineamine (1.15 g); ESI-MS (m/z): 355.1 (M⁺+H).

N-[3-carboxy-phenyl]-4-(2-chloro-3-pyridyl)-2-pyrimidineamine: A mixture of N-[3-ethoxycarbonyl-phenyl]-4-(2-chloro-3-pyridyl)-2-pyrimidineamine (1.15 g, 3.24 mmol), sodium hydroxide (300 mg, 7.5 mmol) in acetonitrile (15 mL) and water (5 mL) is heated to reflux for 4 hours. The reaction mixture is then cooled to room temperature and concentrated. The residue is dissolved in water and acidified with 10% hydrochloric acid. The solid is collected by filtration and washed with water, methanol and dried to give N-[3-carboxy-phenyl]-4-(2-chloro-3-pyridyl)-2-pyrimidineamine (600 mg); ESI-MS (m/z): 327.0 (M⁺+H).

N-[3-carboxy-phenyl]4-[2-(4-amino-butyl-amino)-3-pyridyl]-2-pyrimidine-amine: A mixture of N-[3-carboxy-phenyl]-4-(2-chloro-3-pyridyl)-2-pyrimidineamine (100 mg, 0.31 mmol) in 1,4-diaminobutane (1 mL) is heated to 110° C. for 24 hours. The reaction mixture is then cooled to room temperature and concentrated. The residue is dissolved in water and neutralized with 10% hydrochloric acid. The solid is collected by filtration, washed with water and dried to give N-[3-carboxy-phenyl]-4-[2-(4-amino-butyl-amino)]-3-pyridyl}-2-pyrimidineamine (75 mg); ESI-MS (m/z): 379 (M⁺+H).

Macro-cyclization of N-[3-carboxy-phenyl]-4-[2-(4-amino-butyl-amino)-3-pyridyl]-2-pyrimidineamine: N-[3-carboxy-phenyl]-4-[2-(4-amino-butyl-amino)-4-pyridyl]-2-pyrimidineamine (53 mg, 0.14 mmol) is dissolved in DMF (50 mL) and then treated with diisopropylethylamine (123 µL, 0.7 mmol). This solution is cooled to 0° C., and treated with HATU (79 mg, 0.21 mmol). After stirring for 3 hours, the reaction mixture is concentrated and purified by preparative HPLC to give the desired macrocyclic compound; ESI-MS (m/z): 361 (M⁺+H).

Example 3

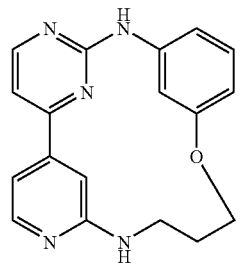

N-[3-methoxy-phenyl]-4-(2-chloro-4-pyridyl)-2-pyrimidineamine: A mixture of 3-dimethylamino-1-(2-chloro-4-pyridyl)-2-propen-1-one (2.22 g, 10.5 mmol), 3-methoxy-phenyl-guanidine nitrite (2.40 g, 10.5 mmol), lithium hydroxide (350 mg, 14.5 mmol) in 2-butanol (25 mL) is heated to reflux for 8 hours. The reaction mixture is cooled to room temperature, concentrated and water (60 mL) is added. The resultant solid is collected by filtration and washed with water, isopropanol and dried to give N-[3-methoxy-phenyl]-4-(2-chloro-4-pyridyl)-2-pyrimidineamine (2.81 g); ESI-MS (m/z): 313 (M⁺+H).

N-[3-methoxy-phenyl]-4-[2-N-(3-hydroxy-1-propyl-amino)-4-pyridyl]-2-pyrimidineamine: A mixture of N-[3-methoxy-phenyl]-4-(2-chloro-4-pyridyl)-2-pyrimidineamine (50 mg, 0.16 mmol) in 3-amino-1-propanol (1 mL) is heated to 180° C. for 30 minutes. The reaction mixture is then cooled to room temperature and concentrated. The resultant residue is dissolved in water and neutralized with 10% hydrochloric acid. The solution is extracted with ethyl acetate (3×75 mL). The combined organic layers are washed with brine, dried over sodium sulfate, filtered and concentrated under reduced pressure to give N-[3-methoxy-phenyl]-4-[2-N-(3-hydroxy-1-propyl-amino)-4-pyridyl]-2-pyrimidineamine, which is used for the next reaction without further purification; ESI-MS (m/z): 352 (M⁺+H).

N-[3-hydroxy-phenyl]-4-[2-N-(3-bromo-propyl-amino)-4-pyridyl]-2-pyrimidine-amine: A mixture of N-[3-methoxy-phenyl]-4-[2-N-(3-hydroxy-1-propyl-amino)-4-pyridyl]-2-pyrimidineamine (45 mg, 0.13 mmol) in 48% (wt) HBr water solution (5 mL) is heated to reflux overnight. The reaction mixture is then cooled to room temperature and concentrated. The resultant residue is used for the next reaction without further purification; ESI-MS (m/z): 400 (M⁺+H).

Macro-cyclization of N-[3-hydroxy-phenyl]-4-[2-N-(3-bromo-propyl-amino)-4-pyridyl]-2-pyrimidineamine:
Crude N-[3-hydroxy-phenyl]-4-[2-N-(3-bromo-propyl-amino)-4-pyridyl]-2-pyrimidineamine is dissolved in acetone (20 mL) and then treated with potassium carbonate (177 mg, 1.28 mmol). This solution is heated to reflux. After stirring for 3 hours, the reaction mixture is concentrated and purified by preparative HPLC to give the desired macrocyclic compound (11 mg); ESI-MS (m/z): 320 (M⁺+H).

Example 4

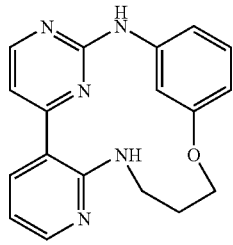

N-[3-methoxy-phenyl]-4-(2-chloro-3-pyridyl)-2-pyrimidineamine: A mixture of 3-dimethylamino-1-(2-chloro-3-pyridyl)-2-propen-1-one (3.50 g, 16.5 mmol), 3-methoxy-phenyl-guanidine nitrite (3.70 g, 16.2 mmol), lithium hydroxide (412 mg, 16.5 mmol) in 2-butanol (15 mL) is heated to reflux overnight. The reaction mixture is cooled to room temperature, concentrated and water (60 mL) is added. The resultant solid is filtered, washed with water, isopropanol and dried to give N-[3-methoxy-phenyl]-4-(2-chloro-3-pyridyl)-2-pyrimidineamine (3.95 g); ESI-MS (m/z): 313 ($M^+$+H).

N-[3-methoxy-phenyl]-4-[2-N-(3-hydroxy-1-propyl-amino)-3-pyridyl]-2-pyrimidineamine: A mixture of N-[3-methoxy-phenyl]-4-(2-chloro-3-pyridyl)-2-pyrimidineamine (91 mg, 0.29 mmol) in 3-amino-1-propanol (1 mL) is heated to 200° C. for 10 minutes. The reaction mixture is then cooled to room temperature and concentrated. The resultant residue is dissolved in water and neutralized with 10% hydrochloric acid. The mixture is extracted with ethyl acetate (3×75 mL). The combined organic layers are washed with brine and dried over sodium sulfate, filtered and concentrated under reduced pressure to give N-[3-methoxy-phenyl]-4-[2-N-(3-hydroxy-1-propyl-amino)-3-pyridyl]-2-pyrimidineamine, which is used for the next reaction without further purification; ESI-MS (m/z): 352 ($M^+$+H).

N-[3-hydroxy-phenyl]-4-[2-N-(3-bromo-propyl-amino)-3-pyridyl]-2-pyrimidine-amine: A mixture of crude N-[3-methoxy-phenyl]-4-[2-N-(3-hydroxy-1-propyl-amino)-3-pyridyl]-2-pyrimidineamine in 48% (wt) HBr water solution (5 mL) is heated to reflux overnight. The reaction mixture is then cooled to room temperature and concentrated. The resultant residue is used for the next reaction without further purification; ESI-MS (m/z): 400 ($M^+$+H).

Macro-cyclization of N-[3-hydroxy-phenyl]4-[2-N-(3-bromo-propyl-amino)-3-pyridyl]-2-pyrimidineamine: Crude N-[3-hydroxy-phenyl]-4-[2-N-(3-bromo-propyl-amino)-3-pyridyl]-2-pyrimidineamine is dissolved in acetone (15 mL), treated with potassium carbonate (140 mg, 1.01 mmol) and heated to reflux. After stirring for 6 hours, the reaction mixture is concentrated and purified by preparative HPLC to give the desired macrocyclic compound (32 mg); ESI-MS (m/z): 320 ($M^+$+H).

Example 5

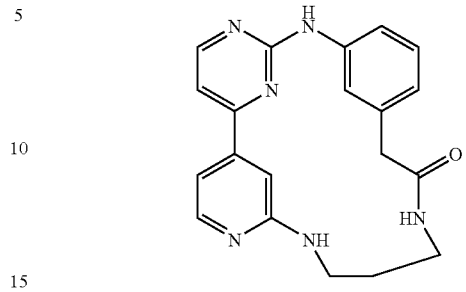

N-[3-carboxymethyl-phenyl]-4-(2-chloro-4-pyridyl)-2-pyrimidineamine: A mixture of 3-dimethylamino-1-(2-chloro-4-pyridyl)-2-propen-1-one (1.05 g, 5.0 mmol), 3-ethoxycarbonylmethyl-phenyl-guanidine nitrite (1.42 g, 5.0 mmol), lithium hydroxide (0.12 g, 5.0 mmol) in 2-butanol (15 mL) is heated to reflux for 24 hours. After cooling to room temperature, the solvent is evaporated under reduced pressure. Water (40 mL) is added and extracted with ethyl acetate (2×50 mL). The combined organic layers are dried over sodium sulfate, filtrated and concentrated. The residue is dissolved in ethanol (30 mL) and treated with lithium hydroxide (0.48 g, 20 mmol). The reaction mixture is heated to reflux for 1 hour. After cooling to room temperature, the mixture is concentrated. The residue is dissolved in water and acidified with 10% hydrochloric acid. The solid is collected by filtration and washed with water, methanol and dried to give N-[3-carboxymethyl-phenyl]-4-(2-chloro-4-pyridyl)-2-pyrimidineamine (1.34 g); ESI-MS (m/z): 341.0 ($M^+$+H).

N-[3-carboxymethyl-phenyl]4-[2-(3-amino-propyl-amino)-4-pyridyl]-2-pyrimidine-amine: A mixture of N-[3-carboxymethyl-phenyl]-4-(2-chloro-4-pyridyl)-2-pyrimidine-amine (118 mg, 0.346 mmol) in 1,3-diaminopropane (2 mL) is heated to 120° C. for 20 hours. After cooling to room temperature, the mixture is concentrated. The residue is dissolved in water and neutralized with 10% hydrochloric acid. Purification by preparative HPLC results in N-[3-carboxymethyl-phenyl]-4-[2-(3-amino-propyl-amino)-4-pyridyl]-2-pyrimidineamine (84 mg); ESI-MS (m/z): 379.1 ($M^+$+H).

Macro-cyclization of N-[3-carboxymethyl-phenyl]-4-[2-(3-amino-propyl-amino)-4-pyridyl]-2-pyrimidineamine: N-[3-carboxymethyl-phenyl]-4-[2-(3-amino-propyl-amino)-4-pyridyl]-2-pyrimidineamine (82 mg, 0.228 mmol) is dissolved in DMF (150 mL) and then treated with diisopropylethylamine (0.091 mL, 0.522 mmol). This solution is cooled to 0° C. and treated with HATU (99 mg, 0.26 mmol). After stirring for 3 hours, the reaction mixture is concentrated and purified by preparative HPLC to give the desired macrocyclic compound (61 mg); ESI-MS (m/z): 361.2 ($M^+$+H).

Example 6

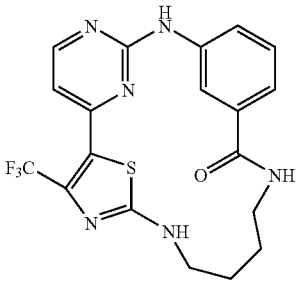

N-[3-ethoxycarbonyl-phenyl]-4-(2-amino-4-trifluoromethyl-5-thiazolyl)-2-pyrimidineamine: A mixture 5-acetyl-2-amino-4-trifluoromethylthiazole (prepared according to wo95/01979) (2.02 g, 9.6 mmol) in N,N-dimethylformamide diethyl acetal (15 mL) is heated to reflux for 3 hours. The reaction mixture is cooled to room temperature, concentrated and hexane (20 mL) is added. The solid is collected by filtration and washed with hexane and dried.

A mixture of the above solid, 3-ethoxycarbonyl-phenyl-guanidine nitrite (2.75 g, 10.2 mmol), lithium hydroxide (240 mg, 10.1 mmol) in 2-butanol (40 mL) is heated to reflux overnight. The reaction mixture is cooled to room temperature, solvent is removed and water (40 mL) is added. The resultant solid is collected by filtration and washed with water, isopropanol and dried to give N-[3-ethoxycarbonyl-phenyl]-4-(2-amino-4-trifluoromethyl-5-thiazolyl)-2-pyrimidineamine (3.5 g); ESI-MS (m/z): 410.1 (M$^+$+H).

N-[3-ethoxycarbonyl-phenyl]-4-[2-(4-t-butoxycarbonylaminobutylamino)-4-trifluoromethyl-5-thiazolyl]-2-pyrimidineamine: t-Butyl nitrite (0.87 mL, 6.54 mmol) is added drop-wise to a suspension of N-[3-ethoxycarbonyl-phenyl]-4-(2-amino-4-trifluoromethyl-5-thiazolyl)-2-pyrimidineamine (1.34g, 3.27 mmol) and anhydrous cupric chloride (925 mg, 6.55 mmol) in acetonitrile (15 mL) over 0.5 hours. After stirring at room temperature for 3 hours, water and chloroform are added and the mixture is made acidic with 12N hydrochloric acid. The layers are separated and the aqueous layer is extracted with chloroform. The combined organic extracts are dried over MgSO$_4$, filtered and concentrated. The residue is purified by chromatography on silica gel to give N-[3-ethoxycarbonyl-phenyl]-4-[2-chloro-4-trifluoromethyl-5-thiazolyl]-2-pyrimidineamine (1.1 g); ESI-MS (m/z): 429 (M$^+$+H).

Diisopropylethylamine (0.1 mL, 0.6 mmol) and 4-t-butoxycarbonylamino-butylamine (25 mg, 1.4 mmol) are added to a solution of N-[3-ethoxycarbonyl-phenyl]-4-[2-chloro-4-trifluoromethyl-5-thiazolyl]-2-pyrimidineamine (52 mg, 0.12 mmol) in 50 mL anhydrous acetonitrile. The mixture is then heated to reflux overnight. The reaction is stopped, cooled to room temperature and concentrated. Water (30 mL) is added and the reaction mixture is extracted with ethyl acetate (3×100 mL). The combined organic layers are dried over MgSO$_4$, filtered and concentrated. The residue is used in the next step without further purification; ESI-MS (m/z): 567.2 (M$^+$+H).

N-[3-carboxyl-phenyl]-4-[2-(4-amino-butylamino)-4-trifluoromethyl-5-thiazolyl]-2-pyrimidineamine: A mixture of crude N-[3-ethoxyl]carbonyl-phenyl]-4-[2-(4-t-butoxycarbonylamino-butylamino)-4-trifluoromethyl-5-thiazolyl]-2-pyrimidineamine (prepared from the previous step), sodium hydroxide (200 mg, 5.0 mmol) in acetonitrile (15 mL) and water (4 mL) is heated to reflux for 4 hours. The reaction mixture is then cooled to room temperature and neutralized with 5% HCl water solution. The reaction mixture is extracted with ethyl acetate (3×75 mL). The combined organic layer is then washed with brine, dried over MgSO$_4$ and concentrated. The resultant crude N-(3-carboxyl-phenyl)-4-[2-(4-t-butoxycarbonylaminobutylamino)-4-trifluoromethyl-5-thiazolyl]-2-pyrimidineamine is used for the next step without further purification; ESI-MS (m/z): 539.2 (M$^+$+H).

Crude N-(3-carboxyl-phenyl)-4-[2-(4-t-butoxycarbonylaminobutylamino)-4-trifluoromethyl-5-thiazolyl]-2-pyrimidineamine is dissolved in 10 mL 1:4 (v/v) mixture of trifluoroacetic acid and dichloromethane and left for 1 hour. Trifluoroacetic acid and dichloromethane are removed to give N-[3-carboxyl-phenyl]-4-[2-(4-amino-butyl amino)-4-trifluoromethyl-5-thiazolyl]-2-pyrimidineamine; ESI-MS (m/z): 439 (M$^+$+H).

Macro-cyclization of N-[3-carboxyl-phenyl]-4-[2-(4-amino-butylamino)-4-trifluoromethyl-5-thiazolyl]-2-pyrimidineamine: Crude N-[3-carboxyl-phenyl]-4-[2-(4-aminobutyl amino)-4-trifluoromethyl-5-thiazolyl]-2-pyrimidineamine (prepared from the previous step) is dissolved in DMF (50 mL) and then treated with diisopropylethylamine (2.1 mL). This solution is cooled to 0° C. and treated with HATU (70 mg, 0.18 mmol). After stirring for 3 hours, the reaction mixture is concentrated and purified by preparative HPLC to give the desired macrocyclic compound; ESI-MS (m/z): 421 (M$^+$+H).

By repeating the procedure described in the above examples, using appropriate starting materials, the following compounds of Formula I are obtained as identified in Table I.

TABLE I

| Example No. | Chemical Structure | Physical Data MS (M + 1) |
|---|---|---|
| 7 | 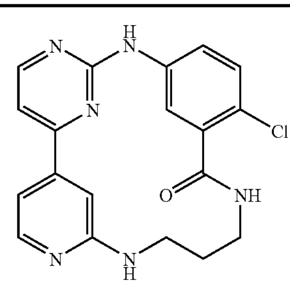 | 381.1 |
| 8 | 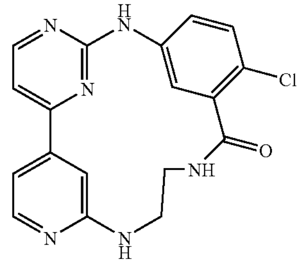 | 367.1 |

TABLE I-continued

| Example No. | Chemical Structure | Physical Data MS (M + 1) |
|---|---|---|
| 9 | 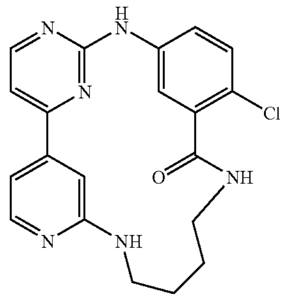 | 395.1 |
| 10 | 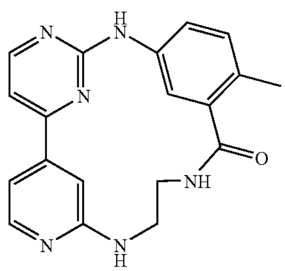 | 347.1 |
| 11 | 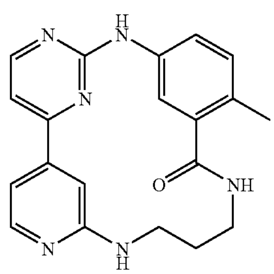 | 361.2 |
| 12 | 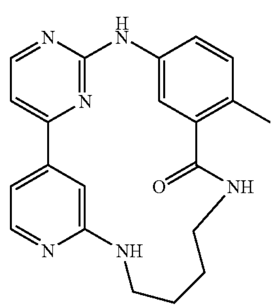 | 375.2 |
| 13 | 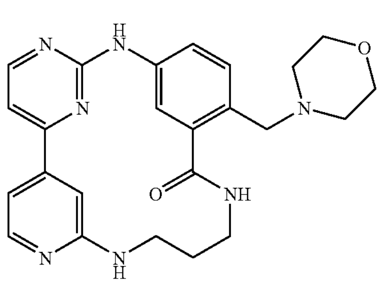 | 446.2 |
| 14 | | 347.1 |
| 15 | | 445.2 |
| 16 | | 347.1 |
| 17 | | 419.2 |
| 18 | | 361.2 |

TABLE I-continued
| Example No. | Chemical Structure | Physical Data MS (M + 1) |
|---|---|---|
| 19 | 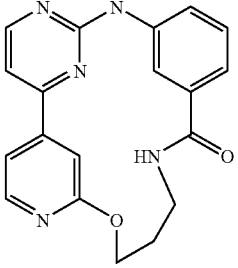 | 348.1 |
| 20 | 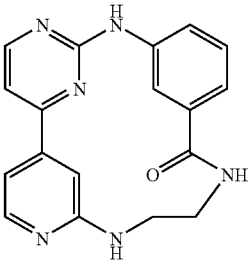 | 333.1 |
| 21 | 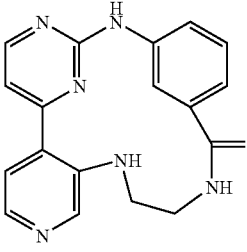 | 333.2 |
| 22 | 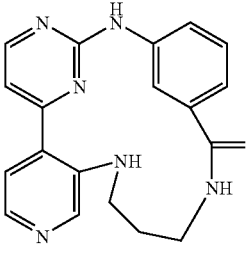 | 347.2 |
| 23 | 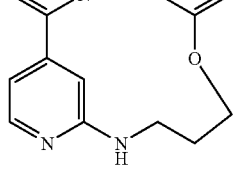 | 320.1 |
| 24 | 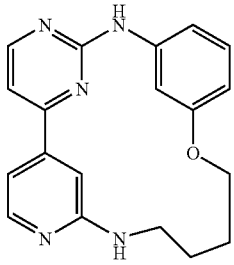 | 334.2 |
| 25 | 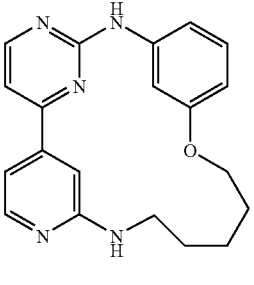 | 348.2 |
| 26 | 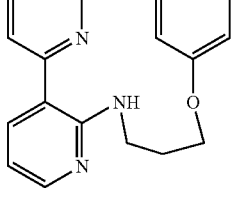 | 320.1 |
| 27 | 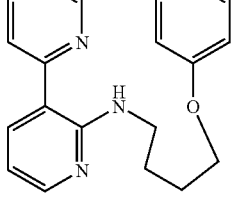 | 334.2 |
| 28 | 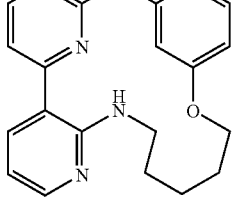 | 348.2 |

TABLE I-continued
| Example No. | Chemical Structure | Physical Data MS (M + 1) |
|---|---|---|
| 29 | 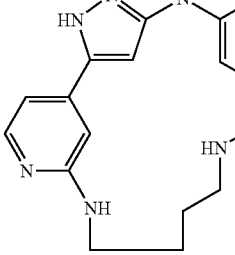 | 319.2 |
| 30 | 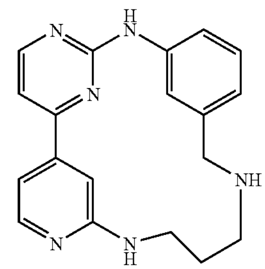 | 333.2 |
| 31 | 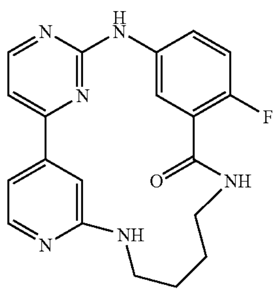 | 379.2 |
| 32 | 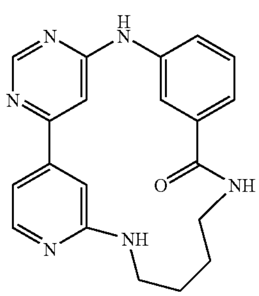 | 361.2 |
| 33 | 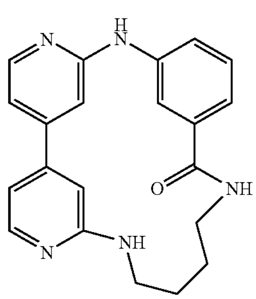 | 360.1 |
| 34 | 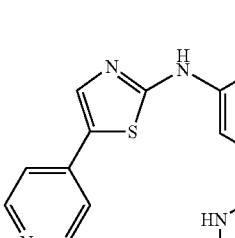 | 349.1 |
| 35 | | 366.1 |
| 36 | | 347.2 |
| 37 | | 347.2 |
| 38 | | 376.2 |

Example 39

Compounds of Formula I Exhibit Biological Activity

The specific activity of compounds of Formula I can be determined to inhibit CDK2 and CDK5 using biological assays known to those of ordinary skill in the art, for example the assays described below:

CDK5 Assay

Solutions of test compounds in various concentrations (33 µM to 0.6 nM) were prepared in assay buffer (50 mM MOPS, pH7.2, 5 mM $MgCl_2$). Recombinant CDK5 (in 5 µl of assay buffer) is added to the wells of a 384 well Proxi-Plate™. A solution (10 µl) containing 1.5 µM ATP, 1.5 µM of biotinylated CDK5 substrate peptide (LCB-AGAKKAVKKTPKKAKKP), 0.01 mCi/ml of [γ-$^{33}$P]-ATP in assay buffer is added to the wells. The reaction is incubated for 60 minutes at room temperature before the addition of stop solution (10 µl of 50 mM ATP, 5 mM of EDTA, 0.1% Triton X-100 and 5 mg/ml streptavadin-PVT beads in PBS). The plates are centrifuged for 2 minutes at 2000 rpm and the scintillation signal is quantified using the TopCount (Packard). $IC_{50}$s are calculated using XLfit software.

CDK2 Assay

A reaction mixture (30 µL) containing ATP (15 µM), [γ-$^{33}$P]-ATP (10 µCi; 3000 Ci/mmol), histone H1 (1 mg/mL), 10 µM or 1 µM test compound (in 1% DMSO) and CDK2/cyclin A (0.007U; Upstate) in assay buffer (50 mM MOPS, pH7.2, 25 mM β-glycerophosphate, 5 mM EGTA, 1 mM sodium orthovanadate and 1 mM dithiothreitol) is dispensed into a 96 well assay plate and incubated for 30 minutes at 30° C. The reaction mixture (25 µL) is transferred with a 96 well dot blotter onto a nitrocellulose filter. After washing three times with 1% phosphoric acid, the [γ-$^{33}$P] incorporation is quantified with Storm® (Molecular Dynamics). Relative activity is compared to maximal enzyme activity and calculated as a percentage (at two different concentrations of test compound).

Cellular Toxicity Assays

Hela (Human adenocarcinoma), 293 (Human Embryonal Kidney), Neuro2a (Murine neuroblastoma), PC-12 (Rat pheochromocytoma) or T98G (Human glioblastoma) cells are plated in to 96 well tissue culture plates at a density of 5,000 or 10,000 cells/well in 50 µL of 10% FCS supplemented media. Test compounds (50 µL at concentrations of 10, 5, 2.5 and 1.25 µM) are added to each well. After incubating the cells for 48 hours at 37° C.-5% $CO_2$, 15 µL of MTT (Promega) is added to each well and the cells are incubated for an additional 5 hours. The optical density at 570 nm is quantified spectrophotometrically.

It is understood that the examples and embodiments described herein are for illustrative purposes only and that various modifications or changes in light thereof will be suggested to persons skilled in the art and are to be included within the spirit and understanding of this application and scope of the appended claims. All publications, patents, and patent applications cited herein are hereby incorporated by reference for all purposes.

We claim:

1. A compound of Formula I:

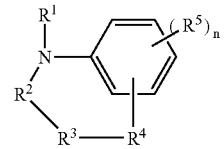

in which n is chosen from 0, 1, 2 and 3;

$R^1$ is chosen from hydrogen and $C_{1-10}$alkyl;

$R^2$ is pyrimidinyl optionally substituted by one to three radicals chosen from halo, $C_{1-10}$alkyl, halo-substituted $C_{1-4}$alkyl, $C_{1-10}$alkoxy and halo-substituted $C_{1-4}$alkoxy; wherein $N(R^1)$ is bonded at the 2 position of pyrimidinyl;

$R^3$ is pyridinyl optionally substituted by one to three radicals chosen from halo, $C_{1-10}$alkyl, halo-substituted $C_{1-4}$alkyl, $C_{1-10}$alkoxy and halo-substituted $C_{1-4}$alkoxy;

$R^4$ is chosen from —$XNR^6(CH_2)_mNR^7C(O)$—, —$XNR^6(CH_2)_mNR^7C(O)CH_2$—, $XNR^6(CH_2)_mNR^7(CH_2)_mNR^7C(O)$—, —$O(CH_2)_mNR^7C(O)$—, —$XNR^6(CH_2)_mO$— and —$XNR^6(CH_2)_mNR^7CH_2$—; wherein X is a bond or $C_{1-4}$alkylene; m is chosen from 1, 2, 3, 4, 5 and 6; $R^6$ and $R^7$ independently are chosen from hydrogen and $C_{1-10}$alkyl; and $R^5$ is chosen from halo, $C_{1-10}$alkyl, halo-substituted $C_{1-4}$alkyl, $C_{1-10}$alkoxy, halo-substituted $C_{1-4}$alkoxy, morpholino-methyl and piperazinyl; wherein any morphlino or piperazinyl of $R^5$ is optionally substituted with a group chosen from halo, $C_{1-6}$alkyl, halo-substituted $C_{1-4}$alkyl, $C_{1-10}$alkoxy, halo-substituted $C_{1-4}$alkoxy and —$XNR^8R^9$, wherein X is a bond or $C_{1-4}$alkylene; $R^8$ and $R^9$ are independently chosen from hydrogen and $C_{1-10}$alkyl optionally substituted by halo or amino; or a salt thereof.

2. A compound of claim 1 in which:

n is chosen from 0, 1 and 2;

$R^1$ is chosen from hydrogen and $C_{1-4}$alkyl;

$R^2$ is pyrimidinyl;

$R^3$ is pyridinyl optionally substituted by one to three radicals chosen from halo, $C_{1-10}$alkyl and halo-substituted $C_{1-4}$alkyl;

$R^4$ is chosen from —$NR^6(CH_2)_mNR^7C(O)$—, —$NR^6(CH_2)_mNR^7C(O)CH_2$—, —$O(CH_2)_mNR^7C(O)$—, —$NR^6(CH_2)_mO$— and —$NR^6(CH_2)_mNR^7CH_2$—; wherein m is chosen from 1, 2, 3, 4 and 5; $R^6$ and $R^7$ independently are chosen from hydrogen and $C_{1-10}$alkyl; and $R^5$ is chosen from halo, $C_{1-10}$alkyl, morpholino-methyl and piperazinyl optionally substituted with $C_{1-6}$alkyl, or —$NR^8R^9$, wherein $R^8$ is hydrogen and $R^9$ is $C_{1-4}$alkyl optionally substituted by halo or amino.

3. A compound of claim 1 in which:

n is chosen from 0 and 1;

$R^1$ is hydrogen;

$R^4$ is chosen from —$NH(CH_2)_mNHC(O)$—, —$NH(CH_2)_m NHC(O)CH_2$—, —$O(CH_2)_mNHC(O)$—, —$NH(CH_2)_mO$— and —$NH(CH_2)_mNHCH_2$—; wherein m is chosen from 1, 2, 3, 4 and 5; and $R^5$ is chosen from halo, $C_{1-10}$alkyl, piperazinyl optionally substituted with $C_{1-4}$alkyl, morpholino-methyl or —NR$^9$R$^{10}$, wherein R$^9$ is hydrogen and R$^{10}$ is ethyl optionally substituted by amino.

4. The compound of claim 1 of the formula Ia:

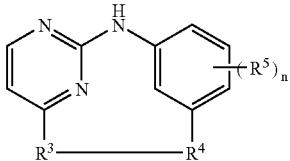

Ia in which n is 0 or 1;

R$^4$ is chosen from —NH(CH$_2$)$_m$NHC(O)—, —NH(CH$_2$)$_m$ NH(CH$_2$)$_m$NHC(O)—, —NH(CH$_2$)$_m$NHC(O)CH$_2$—, —O(CH$_2$)$_m$NHC(O)—, NH(CH$_2$)$_m$O— and —NH(CH$_2$)$_m$NHCH$_2$—; wherein m is chosen from 1, 2, 3, 4 and 5; and R$^5$ is chosen from halo, C$_{1-10}$alkyl, piperazinyl optionally substituted with C$_{1-4}$alkyl, morpholino-methyl or —NR$^9$R$^{10}$, wherein R$^9$ is hydrogen and R$^{10}$ is ethyl optionally substituted by amino.

5. The compound of claim 4 of formula Ib:

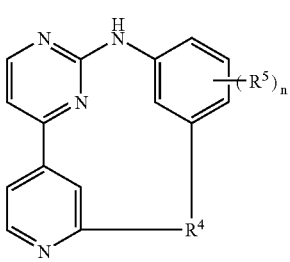

Ib in which n is 0 or 1;

R$^4$ is chosen from —NH(CH$_2$)$_m$NHC(O)—, —NH(CH$_2$)$_m$ NHC(O)CH$_2$—, —O(CH$_2$)$_m$NHC(O)—, —NH(CH$_2$)$_m$ O— and —NH(CH$_2$)$_m$NHCH$_2$—; wherein m is 1, 2, 3, 4 or 5; and R$^5$ is chosen from halo, C$_{1-10}$alkyl, piperazinyl optionally substituted with C$_{1-4}$alkyl, morpholino-methyl or —NR$^9$R$^{10}$, wherein R$^9$ is hydrogen and R$^{10}$ is ethyl optionally substituted by amino.

6. The compound of claim 5 wherein:

n is 0 or 1;

R$^4$ is chosen from —NH(CH$_2$)$_m$NHC(O)—, —NH(CH$_2$)$_m$ NHC(O)CH$_2$—, —O(CH$_2$)$_m$NHC(O)—, —NH(CH$_2$)$_m$ O— and —NH(CH$_2$)$_m$NHCH$_2$—; wherein m is 2, 3, 4 or 5; and R$^5$ is chosen from bromo, chloro, fluoro, methyl, piperazinyl optionally substituted with methyl, morpholino-methyl or —NH(CH$_2$)$_2$NH$_2$.

7. A pharmaceutical composition comprising a therapeutically effective amount of a compound of claim 1 in combination with a pharmaceutically acceptable excipient.

8. A process for preparing a compound of Formula I:

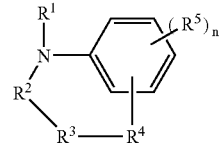

I in which n is chosen from 0, 1, 2 and 3;

R$^1$ is chosen from hydrogen and C$_{1-10}$alkyl;

R$^2$ is pyrimidinyl optionally substituted by one to three radicals chosen from halo, C$_{1-10}$alkyl, halo-substituted C$_{1-4}$alkyl, C$_{1-10}$alkoxy and halo-substituted C$_{1-4}$alkoxy; wherein N(R$^1$) is bonded at the 2 position of pyrimidinyl;

R$^3$ is pyridinyl optionally substituted by one to three radicals chosen from halo, C$_{1-10}$alkyl, halo-substituted C$_{1-4}$alkyl, C$_{1-10}$alkoxy and halo-substituted C$_{1-4}$alkoxy;

R$^4$ is chosen from —XNR$^6$(CH$_2$)$_m$NR$^7$C(O)—, —XNR$^6$(CH$_2$)$_n$NR$^7$C(O)CH$_2$—, XNR$^6$(CH$_2$)$_m$NR$^7$(CH$_2$)$_m$NR$^7$C(O)—, —O(CH$_2$)$_m$NR$^7$C(O)—, —XNR$^6$(CH$_2$)$_m$O— and —XNR$^6$(CH$_2$)$_m$NR$^7$CH$_2$—; wherein X is a bond or C$_{1-4}$alkylene; m is chosen from 1, 2, 3, 4, 5 and 6; R$^6$ and R$^7$ independently are chosen from hydrogen and C$_{1-10}$alkyl; and R$^5$ is chosen from halo, C$_{1-10}$alkyl, halo-substituted C$_{1-4}$alkyl, C$_{1-10}$alkoxy, halo-substituted C$_{1-4}$alkoxy, morpholino-methyl and piperazinyl; wherein any morpholino or piperazinyl of R$^5$ is optionally substituted with a group chosen from halo, C$_{1-6}$alkyl, halo-substituted C$_{1-4}$alkyl, C$_{1-10}$alkoxy, halo-substituted C$_{1-4}$alkoxy and —XNR$^8$R$^9$, wherein X is a bond or C$_{1-4}$alkylene; R$^8$ and R$^9$ are independently chosen from hydrogen and C$_{1-10}$alkyl optionally substituted by halo or amino; said process comprises:

(a) cyclizing a compound of Formula 2, 3, 4 or 5:

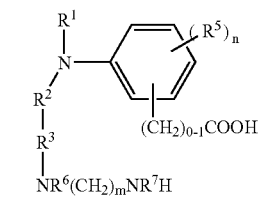

2

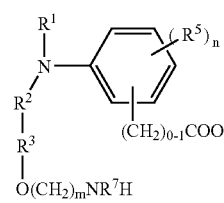

3

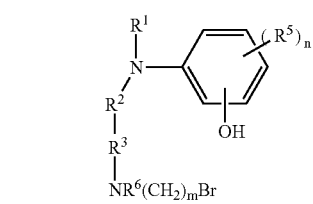

4

-continued

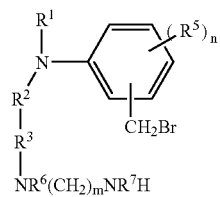

in which m, n, $R^1$, $R^2$, $R^3$, $R^5$, $R^6$ and $R^7$ are as defined in claim 1; or (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

* * * * *